(12) United States Patent
Chebrolu et al.

(10) Patent No.: US 8,992,405 B2
(45) Date of Patent: Mar. 31, 2015

(54) HIGH-SPEED TUMOR SEGMENTATION SYSTEM

(75) Inventors: Venkata Veerendranadh Chebrolu, Andhra Pradesh (IN); Bhudatt R. Paliwal, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 549 days.

(21) Appl. No.: 13/442,606

(22) Filed: Apr. 9, 2012

(65) Prior Publication Data

US 2013/0267755 A1 Oct. 10, 2013

(51) Int. Cl.
*A61N 5/10* (2006.01)
*G06F 19/00* (2011.01)

(52) U.S. Cl.
CPC ............ *G06F 19/321* (2013.01); *A61N 5/1049* (2013.01); *A61N 5/1067* (2013.01); *A61N 2005/1055* (2013.01); *A61N 2005/1061* (2013.01)

USPC .................................... 600/1; 378/65; 378/69

(58) Field of Classification Search
USPC ............... 600/1–8, 411; 378/8, 19–20, 63–69
See application file for complete search history.

(56) References Cited

U.S. PATENT DOCUMENTS 5,673,300 A 9/1997 Reckwerdt et al.
6,385,286 B1 5/2002 Fitchard et al.

OTHER PUBLICATIONS

U.S. Appl. No. 13/173,481, filed Jun. 30, 2011, Tome, Wolfgang Axel, et al., Reduction of Transitivity Errors in Radiotherapy Image Registration.

*Primary Examiner* — John Lacyk
(74) *Attorney, Agent, or Firm* — Boyle Fredrickson, S.C.

(57) ABSTRACT

A system for automatic segmentation of tumor tissue, useful for motion correction during radiotherapy using real-time imaging, identifies multiple regions based on the values of data and then identifies the tumors within the regions based on a priori knowledge about tumor size and/or location. The regions may be refined with robust and fast morphological operations, providing segmentation at speeds commensurate with the motion to be corrected.

20 Claims, 3 Drawing Sheets

HIGH-SPEED TUMOR SEGMENTATION SYSTEM

BACKGROUND OF THE INVENTION

The present invention relates to tumor segmentation in medical imaging with applications in radiation therapy, surgery and chemotherapy, and, in particular, to a method and apparatus for real-time tracking of tumor location for improved radiation therapy.

External beam radiation therapy treats tumor tissues by directing a beam of high-energy radiation into the patient and through the tumor, exploiting increased sensitivity of rapidly dividing tumor cells to radiation damage. Radiation, and radiotherapy, as used herein, will generally be understood to include high-energy electromagnetic radiation, as well as particles such as protons.

The success of external beam radiation therapy is strongly linked to the delivered dose, the latter which is constrained by the need to protect tissue and organs near the tumor. Damage to healthy tissue can be reduced by directing the radiation beam along a number of different axes that all intersect at the tumor while reducing dose to the tissue outside of the intersection. In addition, precise collimation of the radiation beam, for example by computer-controlled shutters, can provide sharp dose gradients at the tumor boundary.

Sophisticated external beam radiation therapies rely on a computerized treatment plan that may be prepared, for example, from images obtained on a CT or MRI machine prior to the radiation treatment. In formulating the plan, the tumor and surrounding healthy tissue are "segmented" into defined volumes and each of the volumes is assigned to a minimum dose (for tumors) or maximum dose (for healthy tissue). The process of segmenting tumor volume can be time-consuming, requiring a healthcare professional to draw boundary lines on multiple image "slices" that together describe a volume of tissue to be treated. Semiautomatic procedures for segmentation are available in which the healthcare professional identifies a "seed" in each volume and the volume is automatically contoured by identifying tissue surrounding the seed that is similar to the seed tissue.

During the radiation treatment, ability to precisely control the dose to the tumor is significantly limited by uncertainties in the position and size of the tumor. "Fractionation", which breaks the radiation therapy into multiple sessions on different days, each delivering a fraction of the total desired dose, may be used to increase the susceptibility of the tumor cells and allow healthy cells to repair between fractions, but can reduce the accuracy of dose placement because of tumor position changes between fractionation sessions. Further, the tumor size may change over time (regression) as a result of the treatment itself.

Even during a particular treatment session, uncertainty in the tumor position can result from periodic organ movements such as those of the heart and lungs or aperiodic motion such as bladder filling.

The problems of tumor motion can be addressed to some extent by monitoring periodic motion (for example with an ECG or respiration sensor) and providing the radiation plan developed for a contour which envelops the tumor motion in all the 10 different phases. Using this approach, a typical radiation plan for lung cancer may include approximately 100 images for each plan. The process of segmenting the tumor in each of these images is extremely time-consuming and prone to error.

A new generation of radiation therapy equipment such as the Renaissance system of ViewRay, Inc. of Cleveland, Ohio provides real-time MR imaging of the patient during the radiation therapy, for example, providing images every quarter second during a 30 seconds to 5 min. radiation therapy session. Ideally, these images could be used to monitor the changing location and position of the tumor during a treatment session. Manual and semiautomatic segmentation is much too slow to exploit this ability. Unfortunately, automatic segmentation techniques such as thresholding, region growing, clustering, and neural networks, have failed to achieve sufficiently accurate or rapid segmentation for real-time tumor segmentation.

SUMMARY OF THE INVENTION

The present invention provides an extremely fast automatic segmentation technique for use with radiation therapy or other applications, and providing real-time medical imaging. The segmentation technique works by dividing the data into multiple regions based on data value similarity. Selected regions are then identified as tumors using an area filtering exploiting rough a priori knowledge about the tumor size optionally augmented by tumor location. Rapid morphological operators are used to generate the multiple regions at speeds allowing real-time tumor motion and deformation correction.

Specifically then, one embodiment of the present invention provides a radiation therapy machine having a radiation delivery system controllable to direct a radiation beam preferentially to a located tumor region during a radiation treatment session and an imaging system operable to image a region of interest holding a tumor at multiple times during the radiation treatment session. An electronic computer receives electronic data representing tissue of the patient and segregates the data according to data values and spatial positions of the data into multiple regions. At least one region is identified as a tumor according to a predetermined tumor characteristic, and then this location is output to the radiation delivery system to change the radiation beam according to that location.

It is thus a feature of at least one embodiment of the invention to provide a segmentation approach that permits real-time correction of the radiation beam during a treatment session. Segregating data according to data values may be performed in a one-pass rapid calculation making the tumor segmentation a simple selection among these regions.

The predetermined tumor characteristic used to select among the regions may be tumor size.

It is thus a feature of at least one embodiment of the invention to identify a simple a priori rule for selecting among the regions. The inventors have recognized that tumor size (when combined with tissue data values) tends to be a robust identifier.

The tumor size may be a single value or a value range.

It is thus a feature of at least one embodiment of the invention to provide a flexible method of identifying tumor size based on either precise measurements or a known range. In real time radiation therapy, for example, there is a need to measure tumor size in real-time to identify changes in tumor volume. In this case, a typical range of tumor size is taken as the input and not the single value of tumor size.

The tumor may be further identified according to a predetermined tumor characteristic of a tumor location.

It is thus a feature of at least one embodiment of the invention to select among identified regions using known location information.

The tumor location may be locations received by the electronic computer or tumor location proximate to a predetermined organ.

It is thus a feature of at least one embodiment of the invention to accept a variety of types of location data including those implicit in the organ being treated.

The step of segregating the data according to data values and spatial positions may divide the data into at least two classifications defined by a predetermined range of data values for a tumor.

It is thus a feature of at least one embodiment of the invention to focus the segmentation process on information about the tumor to provide greatest accuracy in the tumor segmentation.

The data within the predetermined range of data values for a tumor may be subject to morphological processing to eliminate overlap with data outside the predetermined range of data values for a tumor to provide a region related to the tumor and nonoverlapping with other regions.

It is thus a feature of at least one embodiment of the invention to provide isolated regions using extremely fast morphological processing.

The morphological processing performs morphological erosion to eliminate overlap.

It is thus a feature of at least one embodiment of the invention to provide a robust and rapid method for refining the identified regions.

The morphological erosion may be followed by a comparable morphological dilation.

It is thus a feature of at least one embodiment of the invention to provide volume neutral processing to preserve accurate demarcation of the tumor volume.

The radiation therapy machine may output location information which may be either a spatial boundary (including shape and boundary) of the region identified as a tumor or a center point of the region identified as a tumor.

It is thus a feature of at least one embodiment of the invention to provide a flexible output format for different radiation beam correction systems.

The imaging system may be either an MRI machine or data from a CT machine.

It is thus a feature of at least one embodiment of the invention to provide a system suitable for imaging modalities providing data that may be used to demarcate different tissue types.

These particular objects and advantages may apply to only some embodiments falling within the claims and thus do not define the scope of the invention.

DETAILED DESCRIPTION OF THE PREFERRED EMBODIMENT

Hardware

Figure 1:
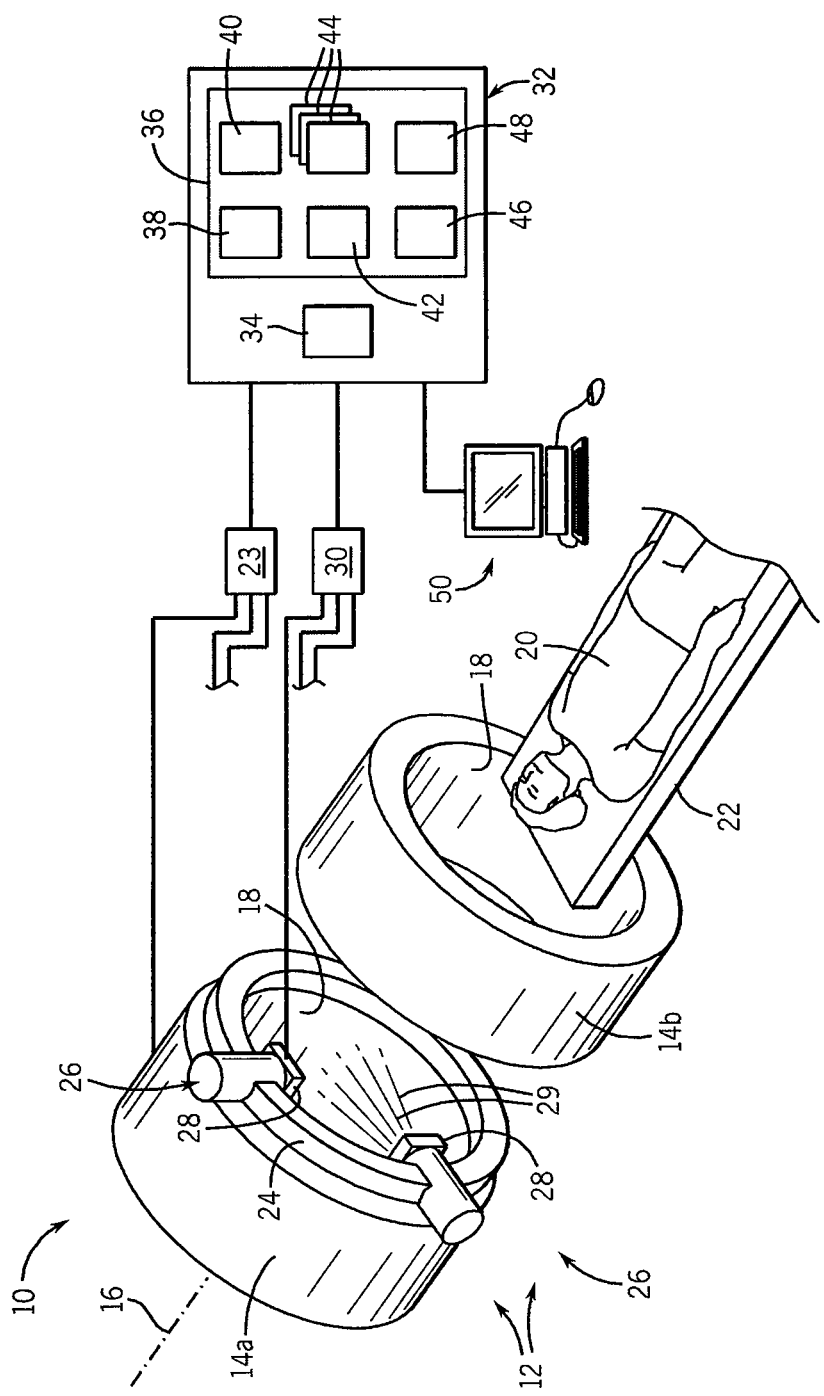
FIG. 1 is a simplified block diagram of a combination radiation therapy and imaging system having a computer system suitable for executing a stored program implementing the present invention.

Referring now to FIG. 1, a combination imaging radiotherapy machine 10 may provide, for example, an MRI magnet assembly 12 having two toroidal magnet elements 14a and 14b spaced along an axis 16 and having aligned bores 18 sized to admit a patient 20 supported on a patient table 22. The magnet elements 14a and 14b may hold a superconducting BO electromagnet and one or more gradient and RF coils as is understood in the art of magnetic resonance imaging. The gradient and RF coils may communicate with an MRI subsystem 23 providing power amplifiers and the like as is also understood in the art.

A radiation therapy gantry 24 may be positioned between the magnet elements 14a and 14b, and may hold one or more radiation delivery systems 26 positioned to rotate about the axis 16 and direct radiation beams 29 toward the patient 20 when the patient 20 is positioned within the MRI magnet assembly 12. Each radiation delivery system 26 may include an electronically controllable collimator 28, for example a multi-leaf collimator controlling an outline of the radiation beam 29 and/or the intensity of different portions of the radiation beam "beamlets". The radiation delivery systems 26 may be accurately positioned in rotation under the guidance of gantry motors and feedback control of position sensors (not shown). The collimators 28 and the gantry motors and position sensors may communicate with a gantry radiation therapy subsystem 30 providing the necessary driving and control electronics to control the multi-leaf collimators 28 and position the gantry 24.

The MRI subsystem 23 and radiation therapy subsystem 30 may in turn be controlled by a system computer 32 having one or more processors 34 communicating with a memory 36. The memory 36 may include radiation therapy control program 38 providing software control of the position of the gantry 24 and the multi-leaf collimators 28 via the gantry radiation therapy subsystem 30 according to techniques well known in the art. This control may follow a stored radiation treatment plan 40 defining intensities of elements of the beamlets of beams 29 at various angles about the axis 16 for treatment of the specific tumor of the patient 20.

The memory 36 may also hold an imaging program 42 which may provide software control of the RF excitation and gradient coil excitation of the MRI magnet assembly 12. The imaging program 42 may further include reconstruction algorithms to generate multiple images 44 defining a volume of the patient 20 receiving radiation treatment, these images reconstructed from received NMR signals obtained from the RF coils. Finally, the memory 36 may hold a segmentation program 46 of the present invention together with data files 48 used by that segmentation program.

The computer 32 may further communicate with a user terminal 50 providing, for example, a graphic display for outputting images and other data and a keyboard or the like for inputting information to any of the programs from an operator.

In an alternative embodiment, the MRI system may be replaced with an x-ray CT system or a megavoltage imaging system using the radiation from the radiation delivery systems 26 and an appropriate portal-imaging device to provide the necessary images. Equipment of this type is well known in the art.

Program Operation

Figure 2:
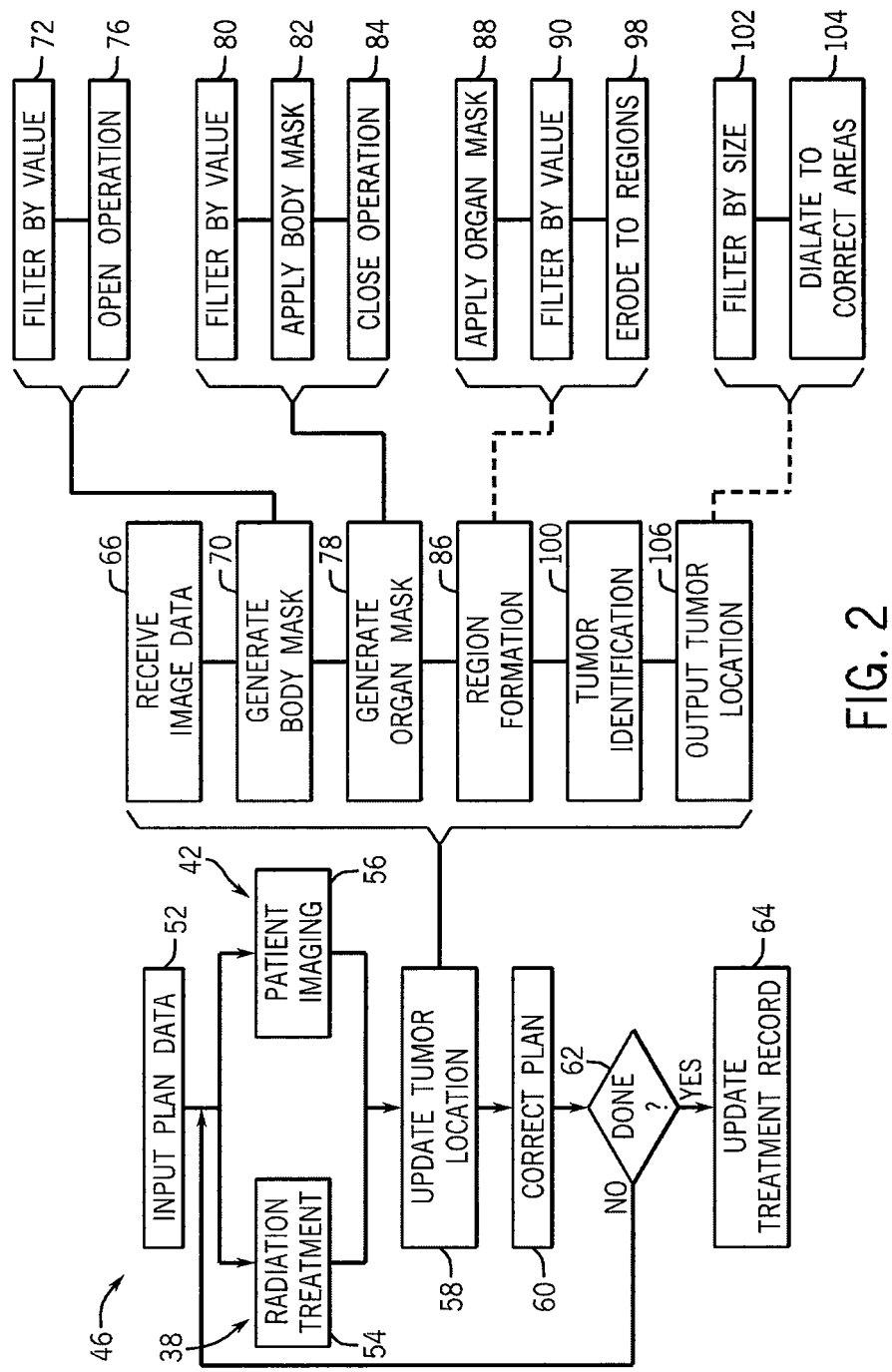
FIG. 2 is a flowchart of the principal steps of one embodiment of the present invention.

Referring now to FIG. 2, the segmentation program 46 may coordinate the radiation therapy control program 38 and imaging program 42 to provide substantially real time correction of the radiation treatment plan 40 based on images 44 obtained from the imaging program 42.

At a first optional process block 52, the segmentation program 46 may receive an input radiation treatment plan 40 that will be used by the radiation therapy control program 38. This radiation treatment plan 40 may provide for a quantitative volume of the tumor, or a range of volumes containing the volume of the tumor and optionally a location of the tumor. The location of the tumor may be a coordinate, for example, with respect to a fiducial point on the patient 20, or a more general indication of tumor proximity to an identifiable organ such as a left or right lung.

After receipt of this data, the radiation therapy control program 38 may initiate a first phase of the radiation treatment plan 40 (separately received by the radiation therapy control program 38) per process block 54 and may further initiate the patient imaging program 42 per process block 56 to collect images of the patient in the vicinity of the tumor. With each execution of process block 54, a portion or phase of the radiation may be delivered that is less than the entire dose intended for the session. With each execution of process block 56, one or more of a set of images 44 defining the volume around the tumor may be obtained.

When an MRI machine is used, the present invention is not limited to a particular imaging sequence but may, for example, use highly constrained back projection (HYPR), for example, as taught by Mistretta Calif., "Under Sampled Radial MR Acquisition and Highly Constrained Back Projection (HYPR) Reconstruction: Potential Medical Imaging Applications in the Post-Nyquist Era, J. Magen. Reson. Imaging 2009; 29:501-516 hereby incorporated by reference. This imaging sequence provides for a rapid image commensurate with the real-time processes of the present invention.

After completion of one execution of process blocks 54 and 56, the program 46 may use the images 44 collected by the patient imaging program 42 to update the tumor location as indicated by process block 58. Updating of the tumor location will be generally understood to be one or more of updating a tumor center location, tumor dimension, or map of a periphery of the tumor.

At succeeding process block 60, the information from the updated tumor location is used to correct the treatment plan 40 to adjust the size of the radiation beam and its location to match the new tumor position. This correction process may, in theory, recalculate the radiation plan based on the new tumor location taking into account the dose that has already been delivered. Alternatively, and for higher-speed, the correction process may directly adjust the sinograms used to drive the multi-leaf collimators 28, for example, as taught by U.S. Pat. Nos. 6,385,286 entitled: "Delivery Modification System for Radiotherapy" and 5,673,300 entitled: "Method of Registering a Radiation Treatment Plan to a Patient" both assigned to the assignee of the present invention and hereby incorporated by reference.

At decision block 62, if the session is not complete, the program loops back to execute process block 54, 56, 58 and 60 again until the full radiation treatment session is complete. At that time, at decision block 62, the program proceeds to process block 64 to update the dose statistics showing cumulative dose to the patient mapped, for example, to the original treatment plan images. This mapping may be performed as taught, for example, in U.S. patent Ser. No. 13/173,481, filed Jun. 30, 2011, and entitled: "Reduction of Transitivity Errors in Radiotherapy Image Registration" assigned to the assignee of the present invention and hereby incorporated by reference.

Referring still to FIG. 2, the above described process of updating the tumor location per process block 58 may begin, as indicated by process block 66, by collecting the data of the images 44 describing the three-dimensional area around the tumor as obtained during execution of process block 56. The images 44 will generally include multiple image "slices" each comprised of multiple data values related to volume elements (voxels) in the patient 20. Each data value is associated with a spatial coordinate in three dimensions, and may represent, for example, proton density or other MRI type values including measures of spin relaxation. The data may be collected from untreated tissue or from contrast agents such as hyperpolarized helium.

Figure 3:
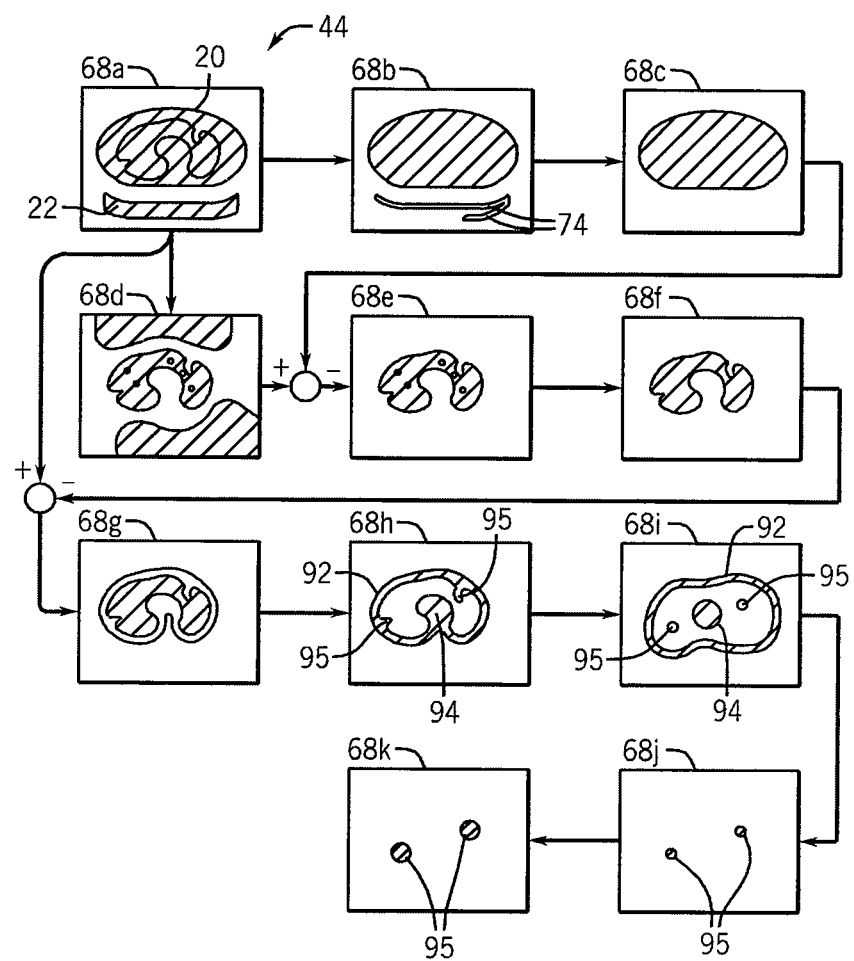
FIG. 3 is a flow diagram depicting the operations of the steps of FIG. 2 by means of simplified two-dimensional images.

Referring now also to FIG. 3, for the purpose of explanation, one slice of image data 68a is depicted being part of a set of slices of the finding volume. Each slice of image data 68 may, for example, be 128×128 voxels and the full set of data may comprise 128 slices displaced along the axis 16 defining a volume of interest. It will be understood that the operations described with respect to an individual slice will be applied to the multiple slices which define a volume of tissue and that the operations will be performed in three dimensions not simply within a given slice The received image data 68a will generally include a cross-sectional image of the patient 20 and of the patient support table 22 as well as additional environmental structures around the patient 20. As shown in FIG. 2, the next step in processing, as represented by process block 70, is the generation of a binary body mask defining portions of these image data 68a describing the body of the patient 20. Generally, this binary body mask 68c (shown in FIG. 3) will have a value of one for all data related to the patient 20 and a value of zero for all data not related to the patient 20. This binary body mask 68c will be used to eliminate data in the images 44 unrelated to the body.

Formation of the binary body mask 68c includes a first step, indicated by process block 72, of filtering image data 68a according to a range of values preselected to predominantly include tissue of the patient 20 and to exclude structure such as the table 22 to produce filtered body data 68b. These range values may be empirically derived and stored in a table or the like or may be developed from a pre-scan of the patient by the imaging system of FIG. 1 or from a treatment planning image input at process block 52. In the event that the treatment-planning image is a different modality than that of the combination imaging radiotherapy machine 10, conversion factors may be employed to generate this range. For different modalities such as CT (x-ray attenuation) and MR (proton density) where there may not be one-to-one mapping between data values of the acquired data, a-priori information from scans of the same modality performed on other patients may be used to obtain a generic range.

This resulting filtered body data 68b (shown in FIG. 3) will include some table structure 74 caused by overlap between value ranges of table structure and body structure inevitable in most imaging modalities.

At succeeding process block 76 (shown in FIG. 2), any background voxels that cannot be reached from the edges of the filtered body data 68b are converted to foreground voxels (data values of zero). Connectivity may be established based on an eight-connected neighborhood described, for example, in Soille P., Morphological Image Analysis: Principles and Applications, Berlin; N.Y.: Springer 2003 hereby incorporated by reference. After this step, a mathematical morphology operation of "opening" is applied to the filtered body data 68b. This process produces the binary body mask 68c eliminating the table structure.

The opening operation is understood to be sequential mathematical operations of dilation and erosion using the same structuring element for both operations and that remove small objects from the "foreground" (in this case being the desired mask of the body) and place them in the "background" (being the non-body portion of the mask). The operation of erosion can be understood as a trimming away of a certain number of voxels around the outer periphery of all foreground objects in an image. In this process, it will be understood that thin foreground objects, such as the table structure 74, will be erased whereas thicker objects, such as the body, will simply have their dimensions reduced.

The succeeding operation of dilation can be understood to be the opposite of erosion and to involve adding a certain number of voxels around the outer periphery of all foreground objects in an image. In this process, the thicker foreground objects will be approximately restored but the thinner foreground objects previously fully eroded during the erosion operation will not be restored.

The number of voxels used in erosion is set to be same as the number of voxels used in dilation so that the resulting foreground objects retain, substantially, their original dimensions.

Referring still to FIGS. 2 and 3, after generation of the binary body mask 68c, a binary organ mask 68f (in this case for lungs) will be generated per process block 78. The particular organ with which the tumor is associated (and the characterization of this mask) may be input by the user as part of process block 52 described above. In this process of generating the binary organ mask 68f, the image data 68a is again filtered as indicated by process block 80 but not for a range that encompasses the entire body (as which produces filtered body data 68b), but using a value range specific to the particular organ such as the lung to produce filtered lung data 68d. These ranges of values for this filtration may again be empirically derived and stored in internal tables or may be obtained from inputs by the user as described above with respect to the binary body mask 68c.

As before with the case with filtered body data 68b, this filtering process will not perfectly identify only the tissue of the lung but will include other non-lung voxels within this image range. In the case of the lung, these other voxels will largely be outside of the body in the air about the patient 20. Accordingly, at process block 82, the body mask 68c may be applied to the filtered lung data 68d (in a logical AND-ing operation) to eliminate voxel data outside of the body producing masked lung data 68e. At this time, those background voxels that are not connected to the edges of the image (as described above) are converted to foreground voxels. The masked lung data 68e will have voids representing voxels that did not fit within the range of the filter range despite their location within the lungs. These voxels are eliminated by a morphometric "close" operation per process block 84 similar to the morphometric open operation but reversing the order of the erosion/dilation to be first dilation and then erosion. The effect is to eliminate small background areas included within foreground areas as opposed to the elimination of small foreground areas within background areas as provided with the open operation. The result of this close operation is to produce a binary organ mask 68f for the lung having a value of one for voxels within the lung and a value of zero for voxels outside of the lung. In this case the dilation may have a larger voxel number than the erosion so as to include a small margin of tissue around the organ of interest.

Alternatively, the binary organ mask 68f may be replaced with a mask in the general known vicinity of the tumor, for example, a sphere about that location (represented as a circle in a given slice).

Referring still to FIGS. 2 and 3, after generation of the binary organ mask 68f per process block 78, a set of disjoint regions will be developed per process block 86. This process again takes the raw image data 68a and applies the binary organ mask 68f to that data to provide tumor region data 68g isolating tissue related to the organ (e.g. lungs) and a small margin of tissue around the organ per process block 88.

The tumor region data 68g is then filtered per process block 90 to identify data values associated with tumor tissue (as opposed to lung tissue) to provide potential tumor data 68h, in this case encompassing a tissue margin around the lungs (lung margin region 92), the heart region 94 and two tumor regions 95 all which have data values within this range because of the similarities of the tissue types and the inclusive breadth of the selected range. Again the range values identifying tumor tissue may be empirically determined and stored in a table, derived from the initial planning image, or input by the user after a prescan using the imaging system of FIG. 1. In this example, the tumors 95 are partially embedded in the wall of the lung forming a continuous region therewith.

The potential tumor data 68h is then eroded per process block 98 to produce disjoint region data 68i which resolves each of the different tissues described above (lung, heart, tumor) in the potential tumor data 68h as isolated regions. The amount of erosion may be determined empirically for a population of individuals and then an average value used.

Each of the separate regions 92, 94, and 95 in the disjoint region data 68i is then enumerated and the volume occupied by each enumerated region determined by a simple addition of the voxels contiguous with each region. The volumes of each region may be identified, for example, using a union-find algorithm, for example, as described by Sedgewick R., Algorithms in C, Reading Mass.: Addison-Wesley 1998 hereby incorporated by reference.

The enumerated regions 92, 94, and 95 may then be analyzed by process block 100 to identify the tumor region 95. This analysis process first identifies only those regions having volumes most closely matching the known volume of the tumor (either input at process block 52 or obtained from a stored table of tumor types sizes). This identification may be supplemented with location data if known. All other regions are then erased.

This process produces tumor region data 68j providing the data only for tumor region 95. At subsequent process block 104, the erosion of process block 98 is reversed through a dilation to restore the tumors to their approximate original size as indicated by tumor image data 68k.

The volume and center point of these volume-restored tumors 95' are then output as indicated by process block 106 where they will be used to correct the treatment plan as has been previously described. Generally the treatment plan will be modified so that the radiation beams maximize the dose to the tumor in its new position. Generally, the tumor location information output at process block 106 may be expressed in a variety of ways including: tumor volume, tumor centroid location or shape or volume of the tumor. This information can be measured in a sequential fashion at different times to provide information about changes in tumor location, volume and shape in real-time, which could be used by radiation therapy planning system to optimize treatment delivery.

The present invention has obtained computational time for auto segmenting a volume of 128×128×128 voxels in 2 seconds, adequate for real-time correction of the treatment plan to accommodate tumor motion. This high-speed segmentation eliminates the need to separately calculate treatment phases and allows the system to work with both periodic and nonperiodic motion.

It should be understood that the present invention is not limited to radiotherapy but may be used in a variety of different applications where tumor size, shape or location need to be monitored or identified, including, for example, in monitoring a patient for surgery or in assessing chemotherapy doses and rates or the effectiveness of chemotherapy treatment.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a computer" and "a processor" or "the microprocessor" can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A radiation therapy machine comprising:
   at least one radiation delivery system controllable to direct a radiation beam preferentially to a located tumor region of a patient during a radiation treatment session;
   an imaging system operable to image a region of interest holding a tumor at multiple times during the radiation treatment session;
   an electronic computer executing a computer program fixed in a non-transient medium to:
   (a) receive electronic data representing tissue of a region of interest of the patient from the imaging system, the electronic data providing data values associated with spatial positions;
   (b) segregate the data according to data values and spatial positions into multiple regions;
   (c) identify at least one region as a tumor according to a predetermined tumor characteristic; and
   (d) output a location of the region identified as a tumor to the radiation delivery system to change the radiation beam according to that location.

2. The radiation therapy machine of claim 1 wherein the predetermined tumor characteristic is tumor size.

3. The radiation therapy machine of claim 2 further including receiving the tumor size as a single value or a range of values.

4. The radiation therapy machine of claim 2 wherein the tumor is further identified according to a predetermined tumor characteristic of a tumor location.

5. The radiation therapy machine of claim 4 wherein the tumor location is selected from a group consisting of locations near a tumor location received by the electronic computer and a tumor location proximate to a predetermined organ.

6. The radiation therapy machine of claim 1 wherein the step of segregating the data according to data values and spatial positions separates the data into at least two classifications defined by a predetermined range of data values for a tumor.

7. The radiation therapy machine of claim 6 wherein data within the predetermined range of data values for a tumor is subject to morphological processing to eliminate overlap with data outside the predetermined range of data values for a tumor to provide a region related to the tumor and nonoverlapping with other regions.

8. The radiation therapy machine of claim 7 wherein the morphological processing performs morphological erosion to eliminate overlap.

9. The radiation therapy machine of claim 8 wherein the morphological erosion is followed by a comparable morphological dilation to maintain a size of the regions.

10. The radiation therapy machine of claim 1 wherein the output of location information is selected from at least one of a spatial boundary of the region identified as a tumor and a center point of the region identified as a tumor.

11. The radiation therapy machine of claim 1 wherein the imaging system is selected from the group consisting of data from an MRI machine and data from a CT machine.

12. A computer program fixed in a non-transient medium and executable on an electronic computer to:
   (a) receive electronic data representing tissue of a region of interest of a patient, the electronic data providing data values associated with spatial positions;
   (b) segregate the data according to data values and spatial positions into multiple regions;
   (c) identify at least one region as a tumor according to a predetermined tumor characteristic; and
   (d) output a location of the region identified as a tumor.

13. The program of claim 12 wherein the predetermined tumor characteristic is tumor size input to the program as size value or range of size values.

14. The program of claim 12 wherein the tumor is further identified according to a predetermined tumor characteristic of a tumor location selected from a group consisting of locations near a tumor location received by the electronic computer and a tumor location proximate to a predetermined organ.

15. The program of claim 12 wherein the step of segregating the data according to data values and spatial positions separates the data into at least two classifications defined by a predetermined range of data values for a tumor.

16. The program of claim 15 wherein data within the predetermined range of data values for a tumor is subject to morphological processing to eliminate overlap with data outside the predetermined range of data values for a tumor to provide a region related to the tumor and nonoverlapping with other regions.

17. The program of claim 16 wherein the morphological processing performs morphological erosion to eliminate overlap.

18. The program of claim 17 wherein the morphological erosion is followed by a comparable morphological dilation to maintain a size of the regions.

19. The program of claim 12 wherein the output of location information is selected from at least one of a spatial boundary of the region identified as a tumor and a center point of the region identified as a tumor.

20. The program of claim 12 wherein the electronic data is selected from the group consisting of data from an MRI machine and data from a CT machine.

* * * * *